United States Patent [19]

Mandell et al.

[11] Patent Number: 4,965,271
[45] Date of Patent: Oct. 23, 1990

[54] METHOD OF INHIBITING THE ACTIVITY OF LEUKOCYTE DERIVED CYTOKINES

[75] Inventors: Gerald L. Mandell, Earlysville; Gail W. Sullivan, Charlottesville, both of Va.; William J. Novick, Lebanon, N.J.

[73] Assignees: Hoechst Roussel Pharmaceuticals, Inc., Somerville, N.J.; University of Virginia, Charlottesville, Va.

[21] Appl. No.: 131,785

[22] Filed: Dec. 11, 1987

Related U.S. Application Data

[63] Continuation-in-part of Ser. No. 947,905, Dec. 31, 1986, abandoned.

[51] Int. Cl.$^5$ .............................................. A61K 31/52
[52] U.S. Cl. ..................................... 514/263; 514/929
[58] Field of Search ................................ 514/263, 929

[56] References Cited

U.S. PATENT DOCUMENTS

| | | | |
|---|---|---|---|
| 4,002,756 | 1/1977 | Higuchi et al. | 514/263 |
| 4,225,607 | 9/1980 | Goring et al. | 514/263 |
| 4,242,345 | 12/1980 | Brenner et al. | 514/263 |
| 4,289,776 | 9/1981 | Mohler et al. | 514/263 |
| 4,291,037 | 9/1981 | Brenner et al. | 514/263 |
| 4,372,959 | 2/1983 | Goring | 514/263 |
| 4,454,138 | 6/1984 | Goring | 514/263 |
| 4,511,557 | 4/1985 | Gauri | 514/263 |
| 4,515,795 | 5/1985 | Hinze et al. | 514/263 |
| 4,576,947 | 3/1986 | Hinze et al. | 514/263 |
| 4,636,507 | 1/1987 | Kreutzer et al. | 514/263 |
| 4,657,910 | 4/1987 | Morgan | 514/263 |
| 4,719,212 | 1/1988 | Goto et al. | 514/263 |
| 4,784,999 | 11/1988 | Angersbach et al. | 514/263 |

FOREIGN PATENT DOCUMENTS

| | | | |
|---|---|---|---|
| 005015 | 10/1979 | European Pat. Off. | 514/263 |
| 173039 | 3/1986 | European Pat. Off. | 514/263 |
| 1441562 | 7/1976 | United Kingdom . | |

OTHER PUBLICATIONS

Sullivan et al., Transact. Assn. Am. Phys., 97: 337–345 (1984).
Furuzawa, S. et al., Chem. Abstracts, 95: 20770t (1981).
Nakayama, T. et al., Bio. Abstracts, 78: 77203 (1984).
Miossec, P. et al., Chem. Abstracts, 101: 168805u (1984).
Kuratsuji, T. et al., Chem. Abstracts, 104: 218828p (1986).

*Primary Examiner*—Olik Chaudhuri
*Assistant Examiner*—E. McAvoy
*Attorney, Agent, or Firm*—Finnegan, Henderson, Farabow, Garrett & Dunner

[57] ABSTRACT

A family of compounds effective in inhibiting interleukin-1 (IL-1) activity, tumor necrosis factor (TNF) activity, and the activity of other leukocyte derived cytokines is comprised of 7-(oxoalkyl) 1,3-dialkyl xanthines of the formula

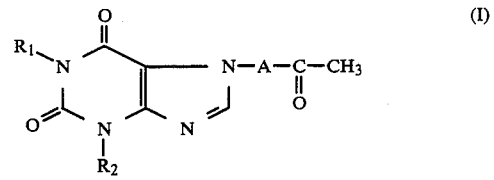

in which $R_1$ and $R_2$ are the same or different and are selected from the group consisting of straight-chain or branched alkyl radicals with 2 to 6 carbon atoms, cyclohexyl, alkoxyalkyl and hydroxyalkyl radicals, and A represents a hydrocarbon radical with up to 4 carbon atoms which can be substituted by a methyl group. The inhibition of Il-1, TNF, and other cytokines in mammals is implicated in allerviation of a wide variety of disease conditions.

14 Claims, 7 Drawing Sheets

EFFECT OF IL-1 (150 UNITS/ml) ON PMN DIRECTED MIGRATION TO FMLP: MODULATION BY DBOPX

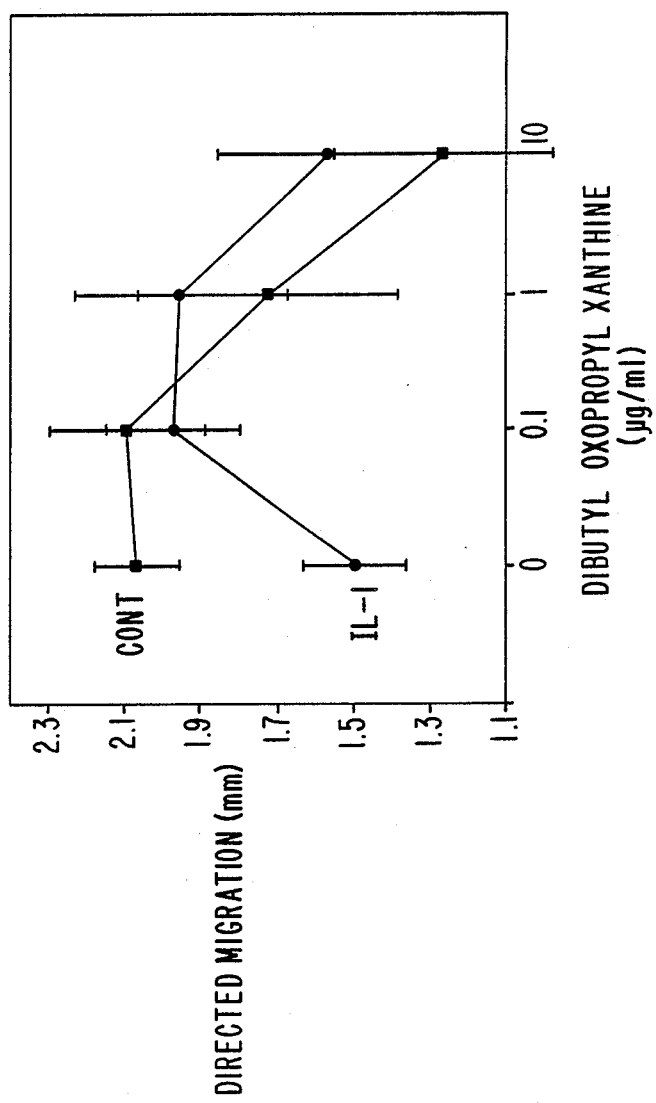

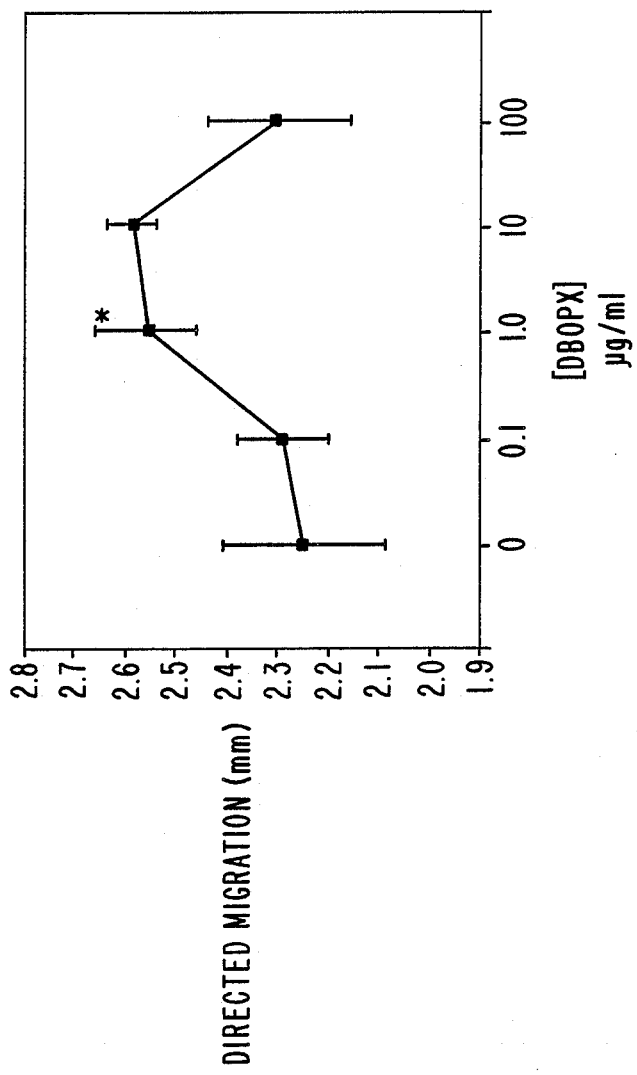

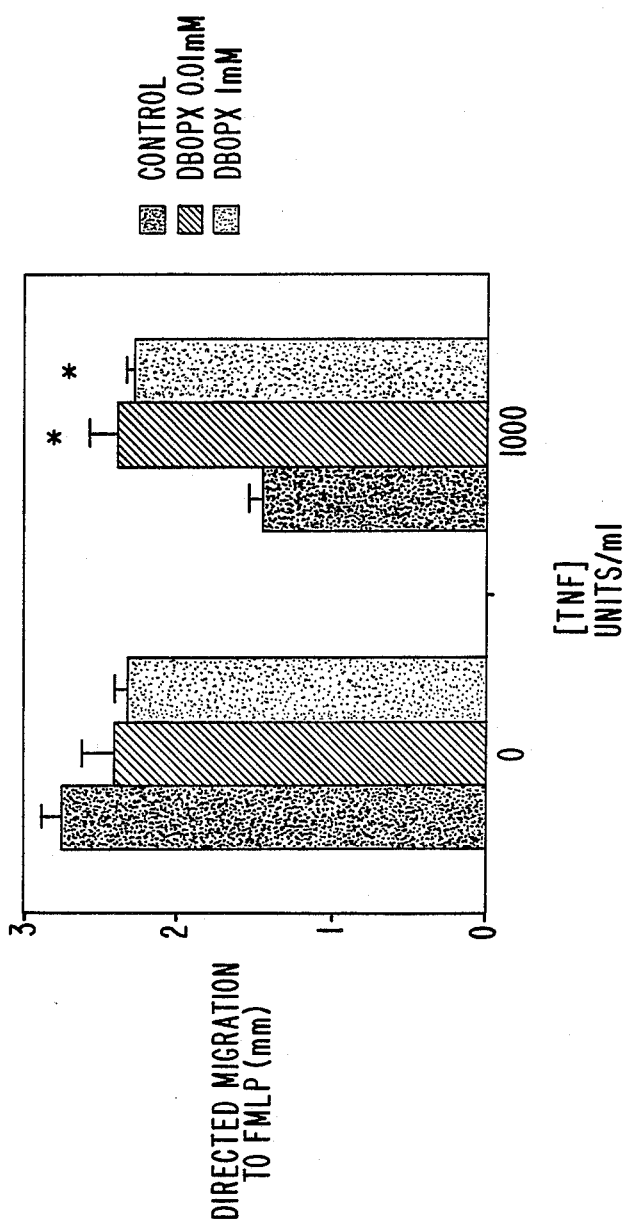

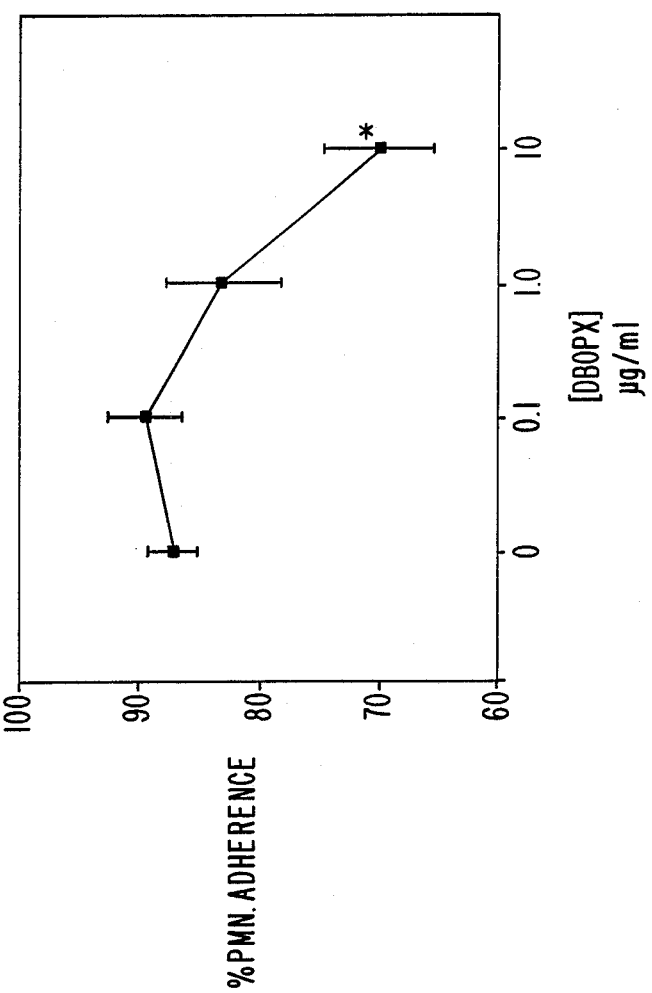

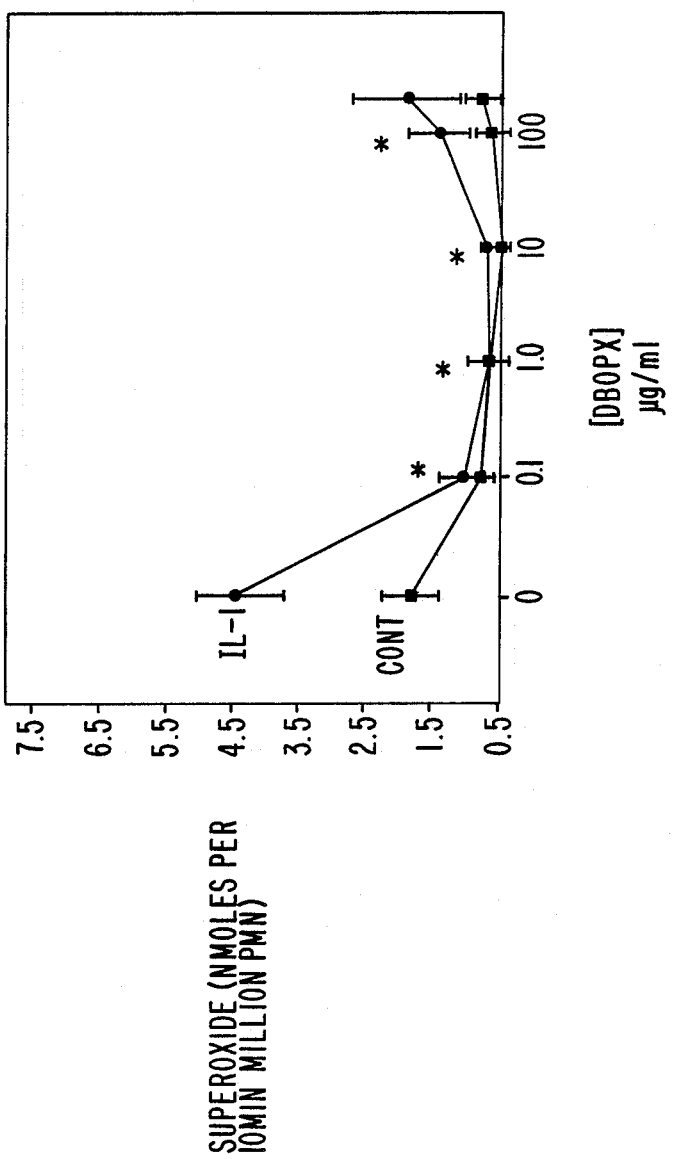

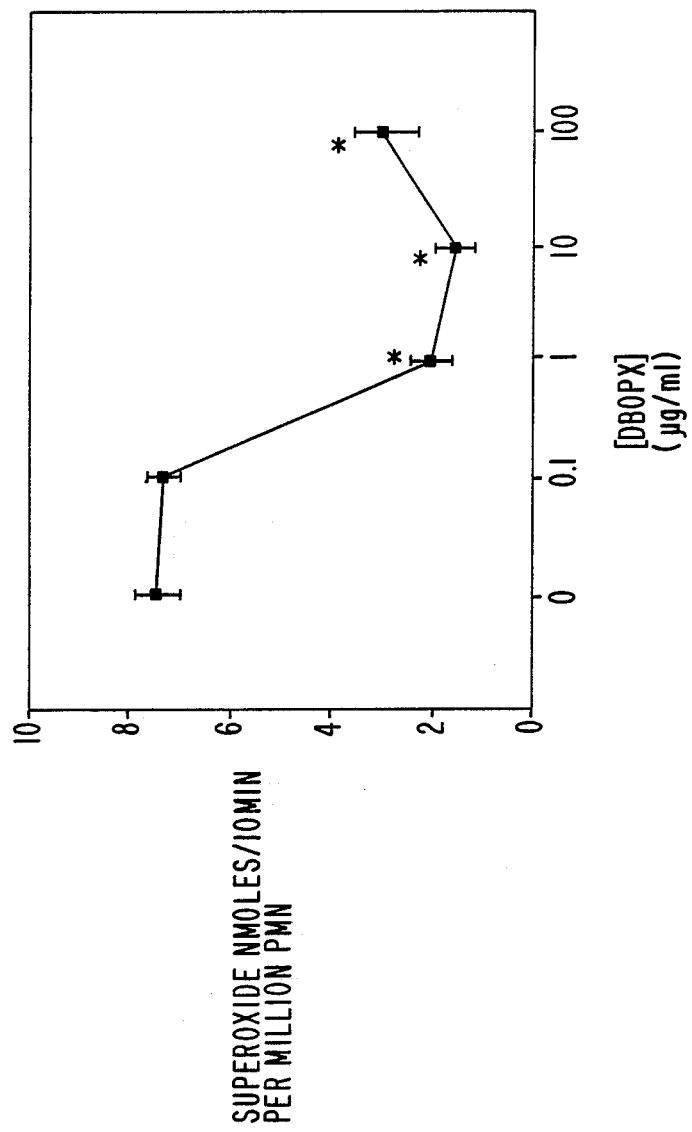

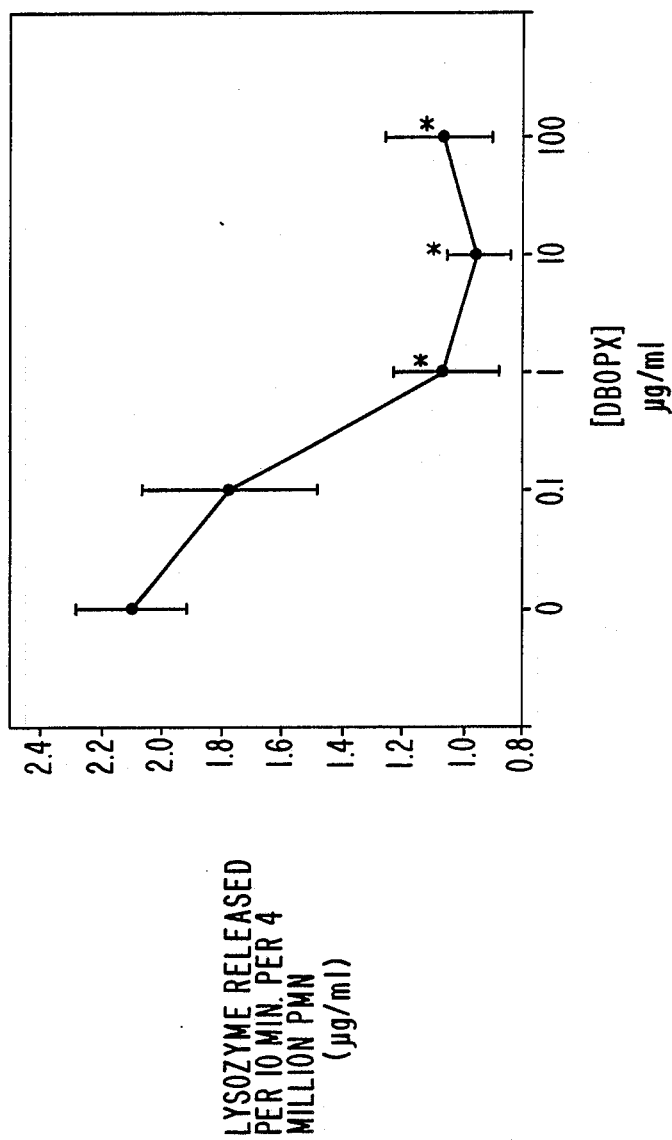

METHOD OF INHIBITING THE ACTIVITY OF LEUKOCYTE DERIVED CYTOKINES

CROSS-REFERENCE TO RELATED APPLICATION

This application is a continuation-in-part of copending application Ser. No. 947,905, filed Dec. 31, 1986, now abandoned for METHOD OF INHIBITING INTERLEUKIN-1 ACTIVITY AND THAT OF OTHER LEUKOCYTE DERIVED CYTOKINES, by Gerald L. Mandell, Gail W. Sullivan, and William J. Novick. The entire disclosure of the related, copending application is relied upon and incorporated by reference herein.

BACKGROUND OF THE INVENTION

This invention relates to the inhibition of activity of leukocyte derived cytokines, such as interleukin-1 and tumor necrosis factor, in humans and mammals. More specifically, this invention provides a method of inhibiting the activity of cytokines to arrest or alleviate certain disease and inflammatory states.

Interleukin-1 (IL-1) and tumor necrosis factor (TNF) are biological substances produced by monocytes and other macrophages in mammals. IL-1 and TNF affect a wide variety of cells and tissues, both in vitro and in vivo. Research has demonstrated that IL-1, TNF, and other leukocyte derived cytokines are important, and even critical, mediators in a wide variety of inflammatory states and diseases. The inhibition of IL-1, TNF, and other leukocyte derived cytokines is of benefit in controlling, reducing, and alleviating many of these conditions.

Detection on and inhibition of IL-1, TNF, and other leukocyte derived cytokines can be relatively easily documented through in vitro analysis of polymorphonuclear neutrophil behavior. Among other activities attributed to IL-1 and other leukocyte derived cytokines is the promotion of leukocyte adherence and the inhibition of neutrophil chemotaxis, both directly contributing to disease and inflammation syndromes.

Despite the desirability of inhibiting the activity of IL-1 and TNF and the activity of other leukocyte derived cytokines and the ease with which inhibition can be detected in vitro, there exists a need in the art for inhibitors of IL-1, TNF, and other cytokines, wherein the inhibitors are acceptable for in vivo administration.

SUMMARY OF THE INVENTION

This invention aids in fulfilling these needs in the art by identifying a class of compounds that can be successfully employed in alleviating conditions caused by, or mediated by, IL-1, TNF, and other leukocyte derived cytokines. The compounds exhibit marked inhibition of cytokine activity, even at low concentrations of the mediators as demonstrated through in vitro tests.

More particularly, this invention provides a method of inhibiting the activity of IL-1, TNF, and other leukocyte derived cytokines in a mammal comprising administering thereto at least one 7-(oxoalkyl) 1,3-dialkyl xanthine of the formula

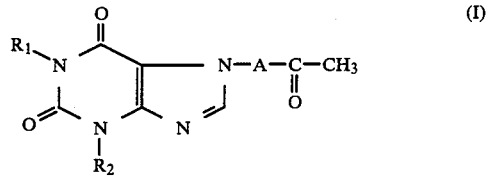

in which $R_1$ and $R_2$ are the same or different and are independently selected from the group consisting of straight-chain or branched-chain alkyl radicals with 2 to 6 carbon atoms, cyclohexyl, straight chain or branched chain alkoxyalkyl, and hydroxyalkyl radicals; and A is a hydrocarbon radical with up to 4 carbon atoms which can be substituted by a methyl group. The xanthine is employed in an amount that is effective in inhibiting the activity of IL-1, TNF, and other leukocyte derived cytokines in the mammal.

BRIEF DESCRIPTION OF THE DRAWINGS

This invention will be more fully described with reference to the drawings in which:

FIG. 1 is a graph showing modulation by 1,3-dibutyl 7-(2-oxopropyl) xanthine (DBOPX) of the effect of interleukin-1 (IL-1) on polymorphonuclear leukocyte (PMN) directed migration to n-formyl methionyl leucyl phenylalanine (FMLP);

FIG. 2 shows the results of modulation by DBPOX of the effect of mononuclear leukocyte LPS stimulated conditioned medium on PMN directed migration to FMLP;

FIG. 3 shows the results of modulation by DBOPX of the effect of tumor necrosis factor (TNF) on PMN directed migration to FMLP;

FIG. 4 shows the results of modulation by DBOPX of LPS stimulated mononuclear leukocyte conditioned medium on PMN adherence to nylon;

FIG. 5 shows the results of modulation by DBOPX of IL-1 on PMN superoxide release stimulated by FMLP;

FIG. 6 is a graph showing modulation by DBOPX of lipopolysaccharide (LPS) stimulated mononuclear leukocyte conditioned medium on superoxide production by PMN stimulated with FMLP; and FIG. 7 is a graph showing modulation by DBOPX of the effect of LPS-stimulated mononuclear leukocyte conditioned medium on lysozyme released by PMN stimulated with FMLP.

DESCRIPTION OF THE PREFERRED EMBODIMENTS

Inhibition of the activity of IL-1, TNF, and other leukocyte derived cytokines can be achieved by the administration of 7-(oxoalkyl) 1,3-dialkyl xanthines to a mammal.

As used herein, the expression "leukocyte derived cytokines" is to be given a broad meaning. Specifically, the term "leukocyte" as used herein means mammalian cells of granulocytic and lymphocytic lineage. Examples of leukocyte cells are polymorphonuclear leukocytes, such as neutrophils, and mononuclear phagocytes, such as monocytes and macrophages and lymphocytes.

The term "cytokine" as used herein means a secretory product of a leukocyte, and in particular a nonantibody protein released by a leukocyte on contact with antigen and which acts as an intercellular mediator of immune response. Examples of cytokines that are within the scope of this invention are chemotactic factors, factors promoting replication of lymphocytes, factors inhibiting replication of lymphocytes, factors affecting macrophage adherence, factors affecting enzyme secretion by macrophages, and factors that mediate secretion of oxidizing agents, such as oxygen, superoxide, hydrogen peroxide and hydroxyl radical.

The 7-(oxoalkyl)1,3-dialkyl xanthines employed in this invention have the following formula:

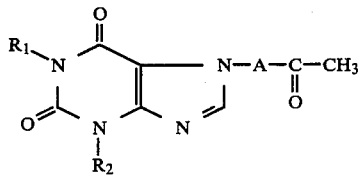

The substituents $R_1$ and $R_2$ in formula (I) are the same or different and are independently selected from the group consisting of straight-chain or branched alkyl radicals with 2 to 6 carbon atoms, cyclohexyl, alkoxyalkyl and hydroxyalkyl radicals. The substituent A represents a hydrocarbon radical with up to 4 carbon atoms, which can be substituted by a methyl group.

A compound that has been found to be particularly effective for inhibiting the effects of IL-1 and other leukocyte derived cytokines on polymorphonuclear leukocytes and monocytes is 1,3-dibutyl 7-(2-oxopropyl) xanthine. This compound, which is also referred to herein in abbreviated form as "DBOPX", has the following formula:

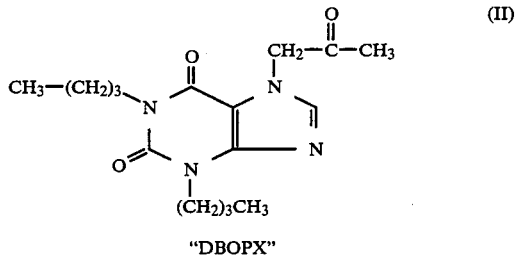

"DBOPX"

The ability of compound (II) to inhibit the effects of IL-1 and other leukocyte derived cytokines on polymorphonuclear leukocyte and monocyte adherence, cell chemotaxis, respiratory (metabolic) burst, and cell degranulation has been demonstrated and is described hereinafter.

Phagocytes important in immunology are polymorphonuclear leukocytes (e.g. neutrophils) and mononuclear phagocytes (e.g. monocytes and macrophages). Phagocyte hypofunction is a cause of recurrent pyogenic infection. To combat pyogenic infection, neutrophils and monocytes respond to chemotactic factors by moving toward the source of infection, where they ingest microorganisms and kill them.

More particularly, a main function of polymorphonuclear leukocytes and monocyte is to kill bacteria and other infectious agents by phagocytosis. The first stage in the ingestion and digestion of a particulate substance by these cells involves the process of bringing the cells and the particles together, usually through chemotaxis. This response is an essential part of host defense against infection. The extensive migration and activity of these cell is manifested by inflammation at the site of injury or invasion of the host.

It has been shown that IL-1 and TNF inhibit chemotaxis by granulocytes, monocytes and macrophages. It has now been discovered that the 7-(oxoalkyl)1,3-dialkyl xanthines of formula (I are capable of modulating the inhibitory effect of IL-1 and TNF on chemotaxis. This has been demonstrated as follows.

The migration of polymorphonuclear leukocytes in response to n-formyl methionyl leucyl phenylalanine (FMLP), a well known chemotactic factor, was determined by chemotaxis under agarose, a well known assay for cell chemotaxis. See *J. of Immunol.*, 115, 6, 1650–1656 (1975). The assay was carried out without IL-1, and the assay was repeated in the presence of IL-1. The assay was also carried out with IL-1, but without DBOPX, and with both IL-1 and DBOPX at DBOPX concentrations of 0.1, 1, and 10 micrograms per milliliter ($\mu$g/ml). The results are depicted in FIG. 1.

As shown in FIG. 1, directed migration of the cells in the absence of IL-1, TNF, and with 0 $\mu$g/ml DBOPX (i.e. "CONT" in FIG. 1) was about 2.08 mm. Directed migration of the cells dropped to about 1.5 mm in the presence of IL-1, TNF, and with 0 $\mu$g/ml DBOPX. Thus, IL-1 inhibited cell chemotaxis directed to FMLP.

FIG. 1 also shows the effect of increasing concentrations of DBOPX on the inhibition of chemotaxis by IL-1. More particularly, DBOPX modulates the inhibitory effect of IL-1 on directed migration to FMLP. Specifically, FIG. 1 shows that DBOPX increased directed migration of the cells and modulated the inhibitory effect of IL-1 at all of the DBOPX concentrations that were evaluated. FIG. 1 also shows that DBOPX was effective in increasing chemotaxis even at very low DBOPX concentrations. Thus, the compounds employed in the process of this invention are particularly effective in modulating the inhibitory effect of IL-1 on cell chemotaxis.

DBOPX is capable of producing a similar effect on polymorphonuclear leukocytes incubated with the products of mononuclear leukocytes that were stimulated with lipopolysaccharide (LPS). These mononuclear cells produce IL-1, TNF, and other inflammatory cytokines. Once again, polymorphonuclear leukocyte directed migration to FMLP was determined by chemotaxis under agarose. The assay was carried out without DBOPX and with concentrations of DBOPX of 0.1, 1.0, 10, and 100 $\mu$g/ml. The results are shown in FIG. 2.

Referring to FIG. 2, the directed migration of the PMN in the conditioned medium containing the inflammatory cultures was about 2.25 mm in the absence of DBOPX. The addition of DBOPX to the medium increased directed migration of the cells at all of the DBOPX concentrations tested. Once again, DBOPX was effective in increasing chemotaxis even at very low concentrations. Moreover, the directed migration was about 2.6 mm at a DBOPX concentration of 10 $\mu$g/ml. By comparison, migration in an unconditioned medium containing LPS was 2.60±0.5mm. (Data not shown in FIG. 2). The probability that DBOPX increased directed migration inhibited by conditioned medium containing inflammatory cultures was 95%.

DBOPX is capable of producing a similar effect on PMN incubated with rh-TNF (alpha). PMN directed migration to FMLP was determined by chemotaxis under agarose. The assay was carried out without DBOPX and with concentrations of DBOPX of 0.01 mM (3.2 μg/ml) and 1 mM (320 μg/ml). The results are shown in FIG. 3.

Referring to FIG. 3, the directed migration of the PMN in medium containing rh-TNF was 1.45 mm in the absence of DBOPX. The addition of DBOPX to the medium increased directed migration of the cells at both of the DBOPX concentrations tested. Once again, DBOPX was effective in increasing chemotaxis even at very low concentrations. By comparison, migration in medium in the absence of TNF was 2.75 mm. The probability that DBOPX increased directed migration inhibited by TNF was better than 95%.

Thus, the 7-(oxoalkyl) 1,3-dialkyl xanthines employed in the process of invention are capable of increasing directional movement of polymorphonuclear leukocytes. These compounds can be administered to a patient to augment chemotactic factors of bacterial or viral origin, or components of plasma activation systems, or factors elaborated by cells of the immune system.

Leukocyte response to an acute inflammatory stimulus involves a complex series of events, including adherence to endothelium near the stimulus. Inhibition of leukocyte adherence can be expected to reduce the degree of inflammation seen in conditions, such a septic shock and adult respiratory distress syndrome. It has been found that the 7-(oxoalkyl) 1,3-dialkyl xanthines employed in this invention effectively block adherence of polymorphonuclear leukocytes.

Specifically, polymorphonuclear leukocyte (PMN) adherence to nylon was determined according to the method of MacGregor et al. New Engl. J. Med. 13:642-646 (1974). Purified PMN cells were incubated with a lipopolysaccharide-stimulated mononuclear leukocyte conditioned medium containing inflammatory cytokines. PMN adherence to nylon was determined without DBOPX, and then with DBOPX at concentrations of 0.1, 1.0, and 10 μg/ml. The percent PMN adherence to nylon was determined for each case. The results are summarized in FIG. 4.

FIG. 4 shows that PMN adherence to nylon in the absence of DBOPX was about 87%. However, when DBOPX was included in the assay at concentrations above about 0.1 μg/ml, PMN adherence to the nylon was inhibited as evidenced by a decline in percent adherence. At a DBOPX concentration of 10 μg/ml, the percent PMN adherence declined to about 70%. The probability that DBOPX decreased adherence of PMN incubated with conditioned medium was 99.7%. Thus, the compounds employed in the process of this invention are particularly effective in blocking adherence of leukocytes and thereby aiding in reducing the degree of inflammation.

Mature phagocytes are in a metabolically dormant state. It is currently believed that recognition of certain objects and substances by phagocytes, such as the attachment of an ingestible particle to the cell surface, changes this situation, and the cell enters a stage of increased metabolic activity, which is referred to as metabolic or respiratory burst. The transition is associated with a series of characteristic changes, including the production of a superoxide anion. Cytokines, such as IL-1 and TNF, are capable of producing a similar effect. In addition to its significance for phagocytic function related to inactivation of ingested microbes, activation of oxygen metabolism is a useful indirect marker for the ingestion process per se. It would be desirable to be able to modulate the effect of cytokines on respiratory burst.

Quantitative methods for direct measurement of hydrogen peroxide and superoxide anions released into the medium are currently available. It has been found that the compounds employed in this invention are capable of modulating respiratory burst in stimulated polymorphonuclear leukocytes (PMN) as determined using these methods.

More particularly, superoxide production was assayed using a modification of the procedure described by Babior et al., J. Clin. Investigation, 52:741-744 (1973). Purified PMN were incubated with an oxidative stimulus with and without IL-1. The medium was assayed for superoxide production. The assay was also carried out without DBOPX and with DBOPX in concentrations of 0.1, 1.0, 10, and 100 μg/ml. The results are shown in FIG. 5.

It is evident from FIG. 5 that about 1.8 nmoles of superoxide/10 min/million PMN were produced by FMLP-stimulated PMN in the absence of IL-1, TNF, and DBOPX (see "CONT" in FIG. 5). Pretreatment with IL-1 (5 units/20 μl), which is known as priming, produced a substantial increase in observed superoxide release to about 4.4 nmoles superoxide/10 min/million PMN.

In contrast, the addition of DBOPX to the assay resulted in a substantial reduction in observed superoxide production as is evident from FIG. 5. Specifically, DBOPX modulated the effect or IL-1 on stimulated PMN at all of the concentrations tested. DBOPX was even effective at a very low concentration of 0.1 μg/ml. The probability that DBOPX decreased superoxide production produced by PMN primed with IL-1, TNF, and stimulated with FMLP compared with IL-1 alone was 95%.

DBOPX is also capable of decreasing superoxide production by PMN primed with LPS-stimulated mononuclear leukocyte conditioned medium containing inflammatory cytokines. This is shown in FIG. 6. Specifically, when PMN were incubated with LPSstimulated mononuclear leukocyte conditioned medium containing inflammatory cytokines and stimulated with FMLP, observed superoxide production in the absence of DBOPX was about 7.4 nmoles/10 min/million PMN. When DBOPX was added to the assay, however, observed superoxide production was lower at all of the DBOPX concentrations tested. Moreover, DBOPX exhibited some effect even at a concentration as low as 1.0 μg/ml. At a DBOPX concentration of 10 μg/ml, superoxide production was about 1.5 nmoles/10 min/million pMN. The probability that DBOPX decreased superoxide production produced by PMN primed with conditioned medium and stimulated with FMLP was 99.5%.

It is evident from these results that the compounds employed in the process of this invention are capable of reducing superoxide production and modulating respiratory burst in phagocytes, such as polymorphonuclear leukocytes and monocytes.

During ingestion, granules in the cytoplasm of the cell fuse with the membrane of a vacuole that was formed around the foreign substance. The granules discharge their contents into the vacuole. Some of this material ends up in the medium surrounding the phagocyte. Since the granules disappear during this process, it is called degranulation. The granule contents include hydrolytic enzymes, lysozyme, bactericidal proteins, and, in the neutrophil, myleoperoxidase.

Degranulation can be assessed by measuring the rate of appearance of granule-associated enzymes in the extracellular medium. In the case of polymorphonuclear leukocytes (PMN), degranulation can be assayed by determining release of lysozyme. It was found that the compounds employed in the process of this invention are capable of modulating the release of lysozyme from stimulated PMN.

More particularly, polymorphonuclear leukocytes (PMN) were incubated with LPS-stimulated mononuclear leukocyte conditioned medium containing inflammatory cytokines. The PMN were then stimulated with FMLP, incubated for a period of time, and lysozyme content was determined in cell supernatant using a well known assay. See *J. Bacteriol.*, 58, 731-736 (1949) The PMN were incubated without DBOPX or with DBOPX in a concentration of 0.1, 1, 10, or 100 µg/ml. The results, which are expressed in terms of lysozyme released/10 min/4 million PMN (µg/ml), are shown in FIG. 7.

Referring to FIG. 7, lysozyme released by PMN primed with LPS-stimulated mononuclear leukocyte conditioned medium (containing inflammatory cytokines) and stimulated with FMLP was about 2 1 µg/ml in the absence of DBOPX. When DBOPX was added to the assay, lysozyme release declined. The decrease was observed at all of the concentrations of DBOPX that were evaluated. Moreover, DBOPX was effective in modulating lysozyme release even at concentrations as low as 0.1 µg/ml. At a DBOPX concentration of 100 µg/ml, the lysozyme release was only about 1.04 µg/ml. The probability that DBOPX inhibited lysozyme release from PMN primed with conditioned medium and stimulated with FMLP was 95%.

It is apparent from these results that the compounds employed in the process of this invention are capable of decreasing the release of lysozyme from PMN primed with LPSstimulated mononuclear leukocyte conditioned medium and then stimulated with FMLP.

In summary, the compounds of formula (I) employed in the process of this invention are capable of modulating the effects of leukocyte derived cytokines, such as interleukin-1 and tumor necrosis factor, on phagocytes, such as polymorphonuclear leukocytes. The compounds are capable of substantially aiding chemotaxis. In addition, the compounds can block adherence of cells. The compounds can decrease oxidative damage to host tissues by phagocytes as evidenced by modulation of respiratory burst in stimulated polymorphonuclear leukocytes. Finally, the compounds can modulate the effects of cytokines on degranulation in stimulated phagocytes. The demonstrated inhibition of IL-1, TNF, and other cytokines by these compounds is suggestive of clinical effectiveness in at least the following areas and conditions.

Because IL-1, TNF, and other leukocyte derived cytokines have been implicated in such a wide variety of mammalian conditions, this invention has a similarly broad scope of application. Among the conditions that can be treated or alleviated by the inhibition of IL-1, TNF, and other leukocyte derived cytokines are: sepsis, septic shock, endotoxic shock, gram negative sepsis, toxic shock syndrome, adult respiratory distress, fever and myalgias due to infection (i.e. influenza), cachexia secondary to infection or malignancy, cachexia secondary to AIDS, rheumatoid arthritis, gouty arthritis, osteoporosis, keloid formation, scar tissue formation, decreased appetite, Crohn's disease, ulcerative colitis, fever due to central nervous system bleeding, glomerulonephritis, multiple sclerosis, Creutzfeld-Jacob disease, adverse reactions to dialysis, diabetes melitus, and psoriasis.

By reference to the specific cause of the disease condition, the more generic term "trauma" can be used. The term "trauma" refers broadly to cellular attack by foreign bodies and physical injury of cells. Included among foreign bodies are microorganisms, particulate matter, chemical agents, and the like. Included among physical injuries are mechanical injuries, such as abrasions, lacerations, contusions, wounds, and the like; thermal injuries, such as those resulting from excessive heat or cold; electrical injuries, such as those caused by contact with sources of electrical potential; and radiation damage caused, for example, by prolonged, extensive exposure to infrared, ultraviolet or ionizing radiations.

Microorganisms included among the foreign bodies that can elicit a biological response are bacilli, fungi and yeast, viruses, parasites, and the like. Representative bacilli are: Actinomyces spp.; Bacteroides spp.; Corynebacterium spp.; Enterobacteriacea; Enterococcus; Haemophilus spp.; Micrococcus spp.; Neissera spp.; *Staphylococcus aureus*; *Streptococcus pneumoniae*; Clostridium spp.; *Streptococrus agalactiae*; Bacillus spp.; *H. influenzae*; Moraxella spp.; Myccbacteria spp.; *Pseudodomonas aeruginosa*; Vibrio spp.; and Mycoplasma.

Representative fungi and yeast that are capable of eliciting a biological response are: Microspurum; Blastomyces; Histoplasma; Aspergillus; Cryptococcus; Candida spp.; Coccidioides; and *Candida albicans*.

Representative viruses are: Rhinovirus; Parainfluenza; Enterovirus; Influenza; Smallpox and vaccinia; Herpes simplex; Measles; Rubella; Arbovirus (Western, Eastern and Venezuelan equine encephalitis, and California encephalitis); Rabies; Colorado tick fever; Yellow fever; Dengue; Hepatitis Virus B (HB Ag); Hepatitis Virus A (HAV); and Human Immunodeficiency Virus (HIV).

Representative parasites that can elicit a response are: Trypanosoma cruzi; Entamoeba histolytica; Leishmania brasiliensis; Leishmania tropica; Leishmania donovani; Toxiplasma gondii; Plasmodium falcipaum; Trypanosoma rhodesiense; Loa loa; Trichomonas hominis; Schistosoma japonicum; Schistosoma mansoni; and Fasciola hepatica.

Particulate materials capable of eliciting a biological response include silica, asbestos, monosodium urate, cotton fibers, coal dust, beryllium, and the like.

Chemical agents include heavy metals, such as lead, chromium, mercury, arsenic, and the like; organic solvents, such as trichloroethylene, and the like; herbicides, such as trichlorophenoxyacetic acid and the like; and pesticides, such as mirex and the like.

In addition, inhibition of IL-1, TNF, and other leukocyte derived cytokines will enhance phagocyte activity in stored blood and blood products.

The compounds employed in this invention will now be described in more detail, and methods for preparing the compounds will be provided.

The process of this invention utilizes 7-(oxoalkyl) 1,3-dialkyl xanthines of formula (I) above. While DBOPX is the particularly preferred xanthine, a number of other compounds can be employed. For example, the xanthines of formula (I) can be substituted by other alkyl groups, or by alkoxy or hydroxyalkyl groups. Suitable alkyl groups include branched and straight chain groups, such as ethyl, propyl, isopropyl, butyl, sec-butyl, tert-butyl, amyl, hexyl, and the like. Alkoxy substituted alkyl groups are branched and straight chain groups containing from 2 to 6 carbon atoms in the combined alkoxy and alkyl groups, including methoxymethyl, amyloxymethyl, methoxyethyl, butoxyethyl, propoxypropyl, and the like. Hydroxyalkyl groups are those containing from 1 to 6 carbon atoms, such as hydroxymethyl, hydroxyethyl, hydroxypropyl, hydroxyhexyl, and the like.

The hydrocarbon group represented by A in formula (I) above are divalent saturated aliphatic hydrocarbon groups, i.e., methylene, ethylene, trimethylene and tetramethylene, which can be substituted on the carbon adjacent the carbonyl group with methyl. Such methyl-substituted groups include ethylidine, 1,2-propylene, and 1,3-butylene groups.

The compounds employed in this invention can be synthesized using known techniques. For example, the compounds can be prepared at elevated temperature, optionally in the presence of a solvent, by reacting correspondingly substituted 1,3-dialkyl xanthines of the formula

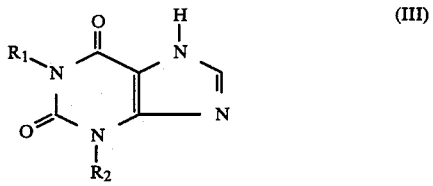

in which $R_1$ and $R_2$ are as defined above with α, β-unsaturated methyl ketones corresponding to the formula

The substituent R in formula (IV) represents hydrogen or a methyl group. The reaction can be conducted in an alkaline medium.

An alternative method of preparation involves reacting alkali metal salts of 1,3-dialkyl xanthine derivatives of general formula II, in which $R_1$ and $R_2$ are as defined above, with oxoalkyl halides corresponding to the formula

in which A is as defined above, and Hal represents a halogen atom, preferably chlorine or bromine.

These reactions are preferably carried out at temperatures in the range from 40° to 80° C., optionally under elevated or reduced pressure, but usually at atmospheric pressure. The individual starting compounds can be employed either in stoichiometric quantities or in excess. The alkali salts in the alternative method of preparation can either be prepared beforehand or in the reaction itself.

Suitable solvents for use in the reactions are water-miscible compounds, preferably lower alcohols, such as methanol, propanol, isopropanol, and various butanols; also acetone; pyridine; triethylamine; polyhydric alcohols, such as ethylene glycol and ethylene glycol monomethyl or monoethyl ether.

The compounds of formula (I) are known for their marked effect in increasing blood flow through skeletal muscle and by their low toxicity. The most active of these compounds for use in accordance with the present invention is 1,3-dibutyl 7-(2-oxopropyl)xanthine, i.e. DBPOX.

A more detailed description of the compounds employed in this invention and methods of preparing the compounds are contained in U.S. Pat. No. 4,242,345, the entire disclosure of which is relied upon and incorporated by reference herein.

Effective amounts of the xanthines can be administered to a subject by any one of various methods, for example, orally as in capsule or tablets, or parenterally in the form of sterile solutions. The xanthines, while effective themselves, can be formulated and administered in the form of their pharmaceutically acceptable addition salts for purposes of stability, convenience of crystallization, increased solubility, and the like.

Preferred pharmaceutically acceptable addition salts include salts of mineral acids, for example, hydrochloric acid, sulfuric acid, nitric acid, and the like; salts of monobasic carboxylic acids, such as, for example, acetic acid, propionic acid, and the like; salts of dibasic carboxylic acids, such as, maleic acid, fumaric acid, oxalic acid, and the like; and salts of tribasic carboxylic acids, such as, carboxysuccinic acid, citric acid, and the like.

The xanthines can be administered orally, for example, with an inert diluent or with an edible carrier. They can be enclosed in gelatin capsules or compressed into tablets. For the purpose of oral therapeutic administration, the compounds can be incorporated with excipients and used in the form of tablets, troches, capsules, elixirs, suspensions, syrups, wafers, chewing gums, and the like. These preparations should contain at least 0.5% of active compound, but the amount can be varied depending upon the particular form and can conveniently be between 4.0% to about 70% of the weight of the unit. The amount of xanthine in such compositions is such that a suitable dosage will be obtained. Preferred compositions and preparations according to the present invention are prepared so that an oral dosage unit form contains between about 1.0 mgs and about 300 mgs of active compound.

Tablets, pills, capsules, troches, and the like can contain the following ingredients: a binder, such as microcrystalline cellulose, gum tragacanth or gelatin; an excipient, such as starch or lactose; a disintegrating agent, such as alginic acid, Primogel, corn starch, and the like; a lubricant, such as magnesium stearate or Sterotes; a glidant, such as colloidal silicon dioxide; a sweetening agent, such as sucrose or saccharin; or flavoring agent, such as peppermint, methyl salicylate, or orange flavoring. When the dosage unit form is a capsule, it can contain, in addition to material of the above type, a liquid carrier, such as a fatty oil.

Other dosage unit forms can contain other materials that modify the physical form of the dosage unit, for example, as coatings. Thus, tablets or pills can be coated with sugar, shellac, or other enteric coating agents. A syrup may contain, in addition to the active compounds, sucrose as a sweetening agent and preservatives, dyes, colorings, and flavors. Materials used in preparing these compositions should be pharmaceutically pure and nontoxic in the amounts used.

For purposes of parenteral therapeutic administration, the xanthines can be incorporated into a solution or suspension. These preparations should contain at least 0.1% of the aforesaid compound, but may be varied between 0.5% and about 50% of the weight thereof. The amount of active compound in such compositions is such that a suitable dosage will be obtained. Preferred compositions and preparations according to the present invention are prepared so that a parenteral dosage unit contains between 0.5 mg to 100 mgs of the active compound.

Solutions or suspensions of the xanthines can also include the following components: a sterile diluent, such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity, such as sodium chloride or dextrose. The parenteral preparation can be enclosed in ampoules, disposable syringes or multiple dose vials made of glass or plastic.

While dosage values will vary with the specific disease condition to be alleviated, good results are achieved when the xanthines of formula (I) are administered to a subject requiring such treatment as an effective oral, parenteral or intravenous dose or from 0.1 to 25 mg/kg of body weight per day. A particularly preferred effective amount is about 1.0 mg/kg of body weight per day. In general, daily dosages will vary from 10–1,000 mg, preferably 100–600 mg per day.

It is to be understood, however, that for any particular subject, specific dosage regimens should be adjusted to the individual need and the professional judgment of the person administering or supervising the administration of the xanthines. It is to be further understood that the dosages set forth herein are exemplary only and that they do not, to any extent, limit the scope or practice of the invention.

This invention will now be described in greater detail in the following Examples.

EXAMPLES

To demonstrate the effectiveness of the claimed invention, a compound of the general formula I was tested to demonstrate inhibition of the activity of both in vitro-generated human IL-1 and other leukocyte derived cytokines, and purified human IL-1. Though a variety of compounds within the general formula (I) are effective in inhibiting the activities of IL-1 and other leukocyte derived cytokines, they will be exemplified with regard to 1,3dibutyl 7-(2-oxopropyl)xanthine (DBPOX) as a particularly preferred form of the invention.

Materials:

The compound 1,3-dibutyl 7-(2-oxopropyl)xanthine (DBOPX) was prepared according to the procedures described in U.S. Pat. No. 4,242,345. Interleukin-1: Purified human monocyte IL-1(IL-1$\beta$), and diluent were purchased from Cistron Biotechnology, Pine Brook, N.J. The human IL-1 used in these experiments was purified human monocyte interleukin-1. The diluent was PBS-0.1% bovine serum albumin (diluent). IL-1 contained <50pg/$\mu$g LPS by limulus amebocyte lysate assay. One LAF unit of IL-1 activity is defined as the amount of IL-1 which causes half-maximal incorporation of 3H-thymidine by murine [C$^3$H]thymocytes in the presence of concanavalin A [0.5 $\mu$g/ml].

Recombinant human tumor necrosis factor (alpha; rh-TNF): The rh-TNF was purchased from Genzyme Corp, (Boston, MA). It was produced in E. coli and was purified by phenyl sepharose chromatography and FPLC to a final purity of greater than 99% as determined by analysis on SDS acrylamide gels stained with both Coomassie Brilliant Blue R250 and silver staining. It has a molecular weight of 36,000 daltons by gel filtration on Superose 12 (FPLC) and consists of 2 dimers of 17,000 daltons each. It was supplied sterile in phosphate-buffered saline containing 0.1% bovine serum albumin as a carrier protein (data supplied by Genzyme). Just before use, the rh-TNF was diluted in Hanks balanced salt solution containing 0.1% human serum albumin.

The other materials were purchased as follows: Dimethyl sulfoxide (DMSO), n-formyl methionyl leucyl phenylalanine (FMLP; 10mM stock solution in DMSO was stored in 20 $\mu$l aliquots at $-70°$ C.), heparin, cytochrome c type VI from horse heart, and superoxide dismutase from bovine liver (SOD; stock solutions at 5 mg/ml in Hanks balanced salt solution were stored in 100 $\mu$l aliquots at 70° C.) (Sigma Chemical, St. Louis, Mo.); Neutrophil isolation medium (NIM: Los Alamos Diagnostics, Inc., Los Alamos, N.M.); Hanks balanced salt solution (HBSS), Minimum essential medium (MEM) and Medium 199 (M199) (Whittaker, M. A. Bioproducts, Walkersville, Md.); Dulbecco's phosphate buffered saline (PBS; GIBCO Laboratories, Grand Island, N.Y.); Limulus Amebocyte Lysate Test (LAL; Associates of Cape Cod, Inc., Woods Hole, Ma.); scrubbed nylon fiber (3 denier type 200) (Fenwal Laboratories, Deerfield, Ill.); Litex and Agarose type HSA (Accurate Chemical and Scientific Corp., Hicksville, N.Y.).

PMN preparation: Purified PMN (98% PMN and <95% viable by trypan blue exclusion) containing <1 platelet per 5 PMN and <50pg/ml LPS (LAL assay) were obtained from normal heparinized (10 Units/ml) venous blood by a one-step ficoll-hypaque separation procedure (NIM). The PMN were washed 3 times with HBSS or MEM. Residual RBC were lysed by hypotonic lysis for the PMN oxidative burst assays.

Mononuclear leukocyte conditioned medium: Mononuclear leukocyte conditioned media was prepared by incubating washed mixed mononuclear leukocytes ($3 \times 10^6$/ml) from NIM separation in medium 199 (M199) containing 10% fresh autologous serum for 18 hrs. at 37° C. (10% $CO_2$) with or without LPS (5ng/ml) in Lab-Tek Flaskettes (Miles Inc., Naperville, Ill.) The suspension was centrifuged 150g $\times$ 10 min., and then the superratant was filtered (0.45 micron pore) and frozen ($-70°$ C.).

Statistics: The results are reported as the mean $\pm$ SEM. Pvalues were determined by using a 2-tailed student t-test.

EXAMPLE 1

Cell Chemotaxis

Chemotaxis under agarose was quantitated by the method of Nelson et al., J. Immunol., 115, 1650–1656 (1975). Purified PMN ($5 \times 10^6$ PMN) were incubated for 15 min. at 37° C. in a total volume of (40ul, 60 $\mu$l, 90 $\mu$l) HBSS with or without DBOPX (as specified) and then were incubated for 30 min. more at 37° C. in a total volume of 0.1 ml with or without LPS (0.2ng/40 μl), LPS stimulated mononuclear leukocyte conditioned medium (40 μl), IL-1 (15 units/60 ul) diluent (60 ul) or rh-TNF (100 units/10 μl). The migration to FMLP (100nM) was measured after 2 hrs. incubation at 37° C.

DBOPX increased chemotaxis inhibited by IL-1, TNF, or LPS stimulated mononuclear leukocyte conditioned medium as shown in FIGS. 1, 2 and 3.

EXAMPLE 2

PMN Adherence To Nylon

PMN adherence was determined by a modified method of MacGregor. Purified PMN were incubated in 0.1 ml medium 199 with or without DBOPX (as specified) containing LPS, or LPS stimulated mononuclear leukocyte conditioned medium for 30 min. at 37° C. After incubation HBSS (0.9 ml) and autologous serum (10 μl) were added to the cell suspensions. The cell suspensions were applied to the top of pre-warmed (37° C.) 60mg nylon columns packed to the 0.3 ml mark on a plastic 1 ml syringe. The columns were allowed to elute for 30 min. at 37° C. and the number of PMN in both the pre- and post-column samples counted. The results are expressed as percent PMN adherence to the nylon.

DBOPX (10 μg/ml) diminished PMN adherence to nylon augmented by LPS stimulated mononuclear leukocyte conditioned medium as shown in FIG. 4.

EXAMPLE 3

PMN Oxidative Burst

Cytochrome c reduction: Purified PMN (2 to $4 \times 10^6$) were suspended in a total volume of 80 ul HBSS with or without DBPOX (as specified) and were incubated for 15 min. at 37° C. with or without SOD (200 units/sample). IL-1 (5 Units/20 μl), LPS (0.1 μg/20 ul), LPS stimulated mononuclear leukocyte conditioned medium (20 μl), or IL-1 diluent were then added and the cells incubated for 30 min. more at 37° C.

HBSS (0.4 ml) and cytochrome c (50 μl; final concentration 120 μM) were added to all samples. FMLP (100μM) was added. The samples were incubated for 10 min. more at 37° C. then iced, and centrifuged ($2000 \times g$ for 10 min.). The optical density of the supernatants was read at a wavelength of 550 nm and the nmoles of SOD-inhibitable superoxide/$10^6$ PMN calculated using the extinction coefficient of $2.11 \times 10^4$ cm$^2$/mmole (reduced-oxidized).

DBOPX (0.1–100 μg/ml) decreased PMN superoxide production when the PMN had been primed with IL-1, TNF, and stimulated with FMLP as is evident from FIG. 5. DBOPX decreased PMN superoxide production when the PMN had been primed with LPS stimulated mononuclear leukocyte conditioned medium as shown in FIG. 6.

EXAMPLE 4

PMN Deqranulation (Release of Lvsozyme)

PMN ($4 \times 10^6$) were suspended in HBSS (0.08 ml) with or without DBOPX (as specified) and incubated for 15 min. (37° C.). Then LPS (0.1 ng/0.02 ml) or LPS stimulated mononuclear leukoycte conditioned medium (0.02 ml) was added to the samples and incubated 30 min. more. HBSS (0.9 ml) and FMLP (10 ul; $10^{-7}$M final concentration) was added to all samples. The samples were incubated for 10 min. and then iced and centrifuged ($2000 \times g$ for 10 min.). The supernatants were poured off and the lysozyme content determined by measurement of changes in the optical density of a suspension of *Micrococcus lysodeikticus* after addition of the supernatants using the method described in *J. Bacteriol.*, 58:731-736 (1949). DBOPX decreased the release of lysozyme from PMN primed with LPS stimulated mononuclear leukocyte conditioned medium and then stimulated with FMLP as is evident from FIG. 7.

Numerous modifications and variations of the present invention are possible in light of the above teachings. It is, therefore, to be understood that within the scope of the appended claims, the invention can be practiced otherwise than as specifically described herein.

What is claimed is:

1. A method of treating a human to inhibit tissue injury accompanying inflammation resulting from leukocyte activity induced by cytokines produced in response to an inflammatory stimulus in the human, wherein the method comprises administering to said human at least one 7(oxoalkyl) 1,3-dialkyl xanthine of the formula

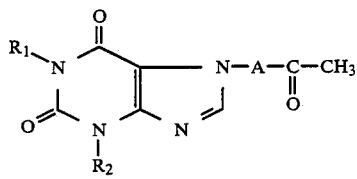

in which
R$_1$ and R$_2$ are the same or different and are selected from the group consisting of straight chain or branched chain alkyl radicals with 2 to 6 carbon atoms, cyclohexyl, straight chain or branched chain alkoxyalkyl and hydroxyalkyl radicals; and A represents a hydrocarbon radical with up to 4 carbon atoms which can be substituted by a methyl group;

wherein said xanthine is administered to said human in an amount sufficient to inhibit activity of human interleukin-1, human tumor necrosis factor, or the activity of other human leukocyte-derived human cytokines on polymorphonuclear leukocytes or monocytes in said human to thereby inhibit said tissue injury.

2. A method of claim 1, wherein said xanthine is 1,3 dibutyl 7-(2-oxo-propyl)xanthine.

3. A method of treating a human to inhibit tissue injury accompanying inflammation resulting from leukocyte activity induced by cytokines produced in response to an inflammatory stimulus in the human, wherein the method comprises administering to said human at least one 7(oxoalkyl) 1,3-dialkyl xanthine of the formula

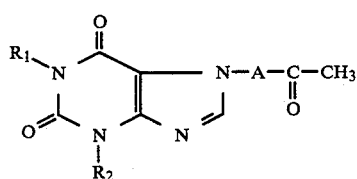

in which $R_1$ and $R_2$ are the same or different and are selected from the group consisting of straight chain or branched chain alkyl radicals with 2 to 6 carbon atoms, cyclohexyl, straight chain or branched chain alkoxyalkyl and hydroxyalkyl radicals; and A represents a hydrocarbon radical with up to 4 carbon atoms which can be substituted by a methyl group;

wherein said xanthine is administered to said human in an amount sufficient to modulate the inflammatory effect of human interleukin-1, human tumor necrosis factor, or other human leukocyte-derived cytokines on polymorphonuclear leukocytes or monocytes by counteracting the inhibitory effect on cell movement in said human.

4. A method of claim 3, wherein said xanthine is 1,3dibutyl 7-(2-oxo-propyl)xanthine.

5. A method of treating a human to inhibit tissue injury accompanying inflammation resulting from leukocyte activity induced by cytokines produced in response to an inflammatory stimulus in the human, wherein the method comprises administering to said human at least one 7(oxoalkyl) 1,3-dialkyl xanthine of the formula

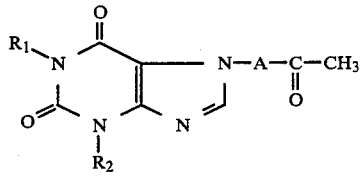

in which $R_1$ and $R_2$ are the same or different and are selected from the group consisting of straight chain or branched chain alkyl radicals with 2 to 6 carbon atoms, cyclohexyl, straight chain or branched chain alkoxyalkyl and hydroxyalkyl radicals; and A represents a hydrocarbon radical with up to 4 carbon atoms which can be substituted by a methyl group;

wherein said xanthine is administered to said human in an amount sufficient to inhibit the stimulatory effect of human interleukin-1, human tumor necrosis factor, or other human leukocyte-derived cytokines or adherence of polymorphonuclear leukocytes or monocytes in said human to thereby inhibit said tissue injury.

6. A method of claim 5, wherein said xanthine is 2,3dibutyl 7-(2-oxo-propyl)xanthine.

7. A method of treating a human to inhibit tissue injury accompanying inflammation resulting from leukocyte activity induced by cytokines produced in response to an inflammatory stimulus in the human, wherein the method comprises administering to said human at least one 7-(oxoalkyl) 1,3-dialkyl xanthine of the formula

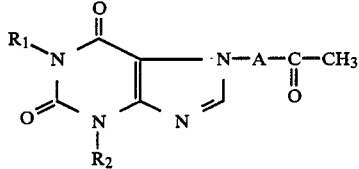

in which $R_1$ and $R_2$ are the same or different and are selected from the group consisting of straight chain or branched chain alkyl radicals with 2 to 6 carbon atoms, cyclohexyl, straight chain or branched chain alkoxyalkyl and hydroxyalkyl radicals; and A represents a hydrocarbon radical with up to 4 carbon atoms which can be substituted by a methyl group;

wherein said xanthine is administered to said human in an amount sufficient to inhibit stimulatory effect of human interleukin-1, human tumor necrosis factor, or other human leukocyte-derived human cytokines n oxidative burst of stimulated polymorphonuclear leukocytes in said human to thereby inhibit said tissue injury.

8. A method of claim 7, wherein said xanthine is 1,3dibutyl 7-(2-oxo-propyl)xanthine.

9. A method of treating a human to inhibit tissue injury accompanying inflammation resulting from leukocyte activity induced by cytokines produced in response to an inflammatory stimulus in the human, wherein the method comprises administering to said human at least one 7(oxoalkyl) 1,3-dialkyl xanthine of the formula

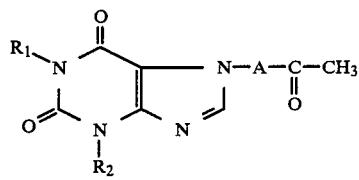

in which $R_1$ and $R_2$ are the same or different and are selected from the group consisting of straight chain or branched chain alkyl radicals with 2 to 6 carbon atoms, cyclohexyl, straight chain or branched chain alkoxyalkyl and hydroxyalkyl radicals; and A represents a hydrocarbon radical with up to 4 carbon atoms which can be substituted by a methyl group;

wherein said xanthine is administered to said human in an amount sufficient to inhibit the activity of human interleukin-1, human tumor necrosis factor, or other human leukocyte-derived human cytokine on degranulation of stimulated polymorphonuclear leukocytes in said human to thereby inhibit said tissue injury.

10. A method of claim 9, wherein said xanthine is 1,3dibutyl 7-(2-oxo-propyl)xanthine.

11. A method of treating a human to inhibit tissue injury accompanying inflammation resulting from leukocyte activity induced by cytokines produced in response to an inflammatory stimulus in the human, wherein the method comprises administering to said human at least one 7(oxoalkyl) 1,3-dialkyl xanthine of the formula

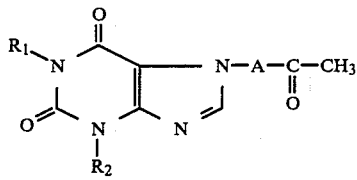

in which
R₁ and R₂ are the same or different and are selected from the group consisting of straight chain or branched chain alkyl radicals with 2 to 6 carbon atoms, cyclohexyl, straight chain or branched chain alkoxyalkyl and hydroxyalkyl radicals; and A represents a hydrocarbon radical with up to 4 carbon atoms which can be substituted by a methyl group;

wherein said xanthine is administered to said human in an amount sufficient to inhibit the effect of human interleukin-1 or human tumor necrosis factor on oxidative burst or degranulation of stimulated neutrophils in said human to thereby inhibit said tissue injury.

12. A method of claim 11, wherein said xanthine is 1,3-dibutyl 7-(2-oxo-propyl)xanthine.

13. A method of treating a human to alleviate inflammatory pathological effects of sepsis, septic shock, endotoxic shock, gram-negative sepsis, toxic shock syndrome, the adult respiratory syndrome, and the fever and cachexia of AIDS, wherein the method comprises administering to said human at least one 7-(oxoalkyl) 1,3-dialkyl xanthine of the formula

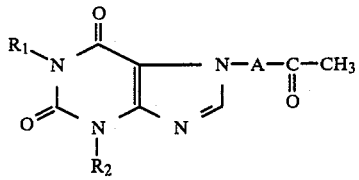

in which
R₁ and R₂ are the same or different and are selected from the group consisting of straight-chain or branched chain alkyl radicals with 2 to 6 carbon atoms, cyclohexyl, straight-chain or branched chain alkoxyalkyl and hydroxyalkyl radicals; and A represents a hydrocarbon radical with up to 4 carbon atoms which can be substituted by a methyl group;

wherein said xanthine is administered to said human in an amount sufficient to inhibit activity of human interleukin-1, human tumor necrosis factor, or the activity of other human leukocyte-derived human cytokines on polymorphonuclear leukocytes or monocytes in said human to thereby inhibit said effects.

14. A method of claim 13, wherein said xanthine is 1,3-dibutyl 7-(2-oxo-propyl)xanthine.

* * * * *